(12) United States Patent
Wang

(10) Patent No.: US 9,090,666 B2
(45) Date of Patent: Jul. 28, 2015

(54) LENSED OPTICAL FIBER FOR ILLUMINATING CAPILLARY TUBE

(76) Inventor: Tiansong Wang, Shoreline, WA (US)

( * ) Notice: Subject to any disclaimer, the term of this patent is extended or adjusted under 35 U.S.C. 154(b) by 105 days.

(21) Appl. No.: 13/534,498

(22) Filed: Jun. 27, 2012

(65) Prior Publication Data

US 2014/0003081 A1  Jan. 2, 2014

(51) Int. Cl.

| F21V 7/04 | (2006.01) |
|---|---|
| G02B 6/00 | (2006.01) |
| G02B 6/036 | (2006.01) |
| G09F 13/00 | (2006.01) |
| C07K 1/26 | (2006.01) |
| G01N 27/447 | (2006.01) |
| G02B 6/26 | (2006.01) |

(52) U.S. Cl.
CPC ............. C07K 1/26 (2013.01); G01N 27/44721 (2013.01); G02B 6/262 (2013.01)

(58) Field of Classification Search
CPC .. G02B 6/262; G02B 6/4203; A61B 5/14546; G01N 21/474; G01N 2021/4742; G01N 2021/4752; G01N 2021/4757; G01N 27/44721
USPC .......... 362/551–582; 359/341.1; 385/127, 123
See application file for complete search history.

(56) References Cited

U.S. PATENT DOCUMENTS

| 3,910,677 | A | | 10/1975 | Becker et al. |
|---|---|---|---|---|
| 5,037,199 | A | | 8/1991 | Hlousek |
| 5,239,360 | A | | 8/1993 | Moring et al. |
| 5,312,535 | A | * | 5/1994 | Waska et al. ................. 204/603 |
| 5,455,879 | A | | 10/1995 | Modavis et al. |
| 5,764,840 | A | * | 6/1998 | Wach ............................ 385/123 |
| 5,845,024 | A | * | 12/1998 | Tsushima et al. .............. 385/33 |
| 5,901,261 | A | * | 5/1999 | Wach .............................. 385/38 |
| 6,137,938 | A | * | 10/2000 | Korn et al. ................... 385/123 |
| 6,238,102 | B1 | * | 5/2001 | Ohtani et al. ................... 385/78 |
| 6,317,550 | B2 | * | 11/2001 | Irie et al. ....................... 385/123 |
| 6,366,726 | B1 | * | 4/2002 | Wach et al. ................... 385/115 |
| 6,597,835 | B2 | | 7/2003 | Jie et al. |
| 6,822,190 | B2 | * | 11/2004 | Smithson et al. ......... 219/121.69 |
| 6,888,628 | B2 | * | 5/2005 | Carrillo ......................... 356/246 |
| 7,151,604 | B2 | * | 12/2006 | Saccomanno et al. ........ 356/343 |
| 7,262,847 | B2 | * | 8/2007 | Goodall et al. ............... 356/344 |
| 7,295,729 | B2 | * | 11/2007 | Cheng et al. .................... 385/33 |
| 7,421,186 | B2 | * | 9/2008 | Boutoussov et al. .......... 385/146 |
| 7,957,002 | B2 | * | 6/2011 | Tsukii et al. .................. 356/436 |
| 2002/0031300 | A1 | * | 3/2002 | Jie et al. .......................... 385/33 |
| 2010/0140505 | A1 | * | 6/2010 | Pang et al. ................... 250/459.1 |
| 2010/0163715 | A1 | * | 7/2010 | Gorfinkel et al. ......... 250/227.28 |

OTHER PUBLICATIONS

Bruno A.E. et al. "Theoretical considerations on the design of cylindrical flow cells utilizing optical fibres" Analytica Chimica Acta 234 (1990) 259-262.

* cited by examiner

Primary Examiner — Jong-Suk (James) Lee
Assistant Examiner — Erin Kryukova
(74) Attorney, Agent, or Firm — David Pressman

(57) ABSTRACT

An optical fiber (500) illuminates the bore (520) of a capillary tube (515) that is used for separating chemicals by capillary electrophoresis (CE). The fiber terminates in either two sloped regions (525) and a curved region (530) or two sloped regions (705) and a flat region (700). Light from these regions is focused on the bore of the capillary tube. Since the fiber is sized to illuminate the core of a CE capillary, it is larger than fibers used in telecommunications and its sloped regions are at angles that would be unsuitable for use in telecommunications. The relatively large diameter of the capillary permits efficient use of a light source (905).

17 Claims, 3 Drawing Sheets

Figure 5:
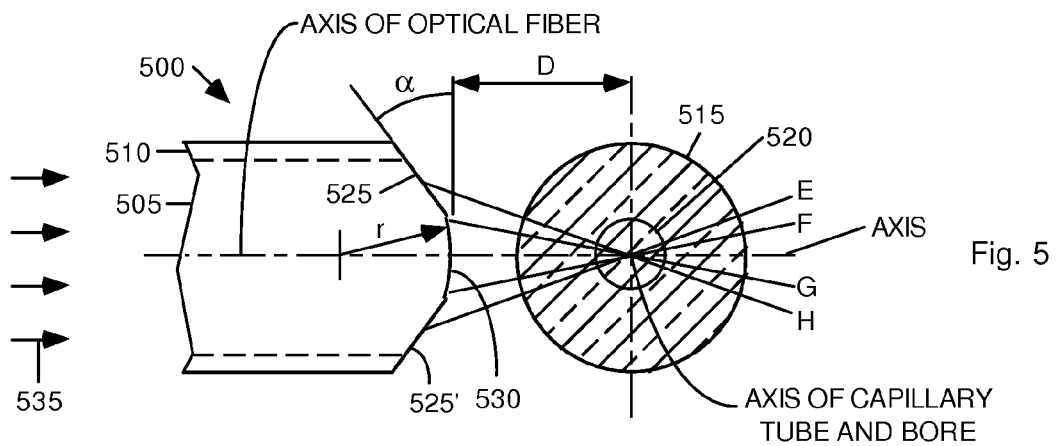

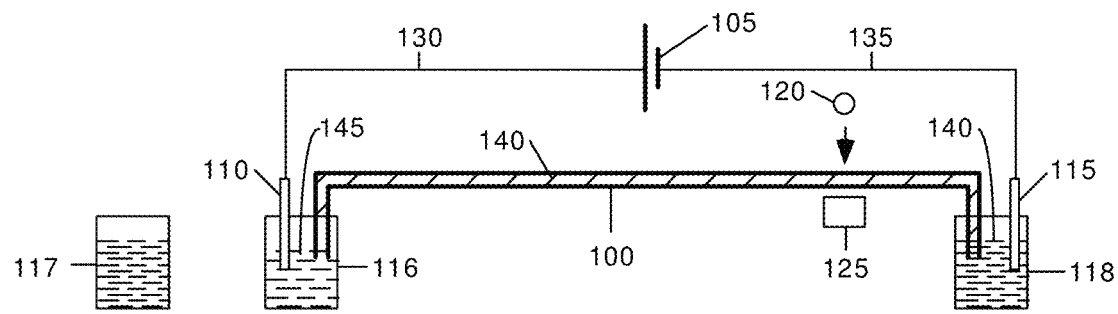
Fig. 1--Prior Art--Load Sample
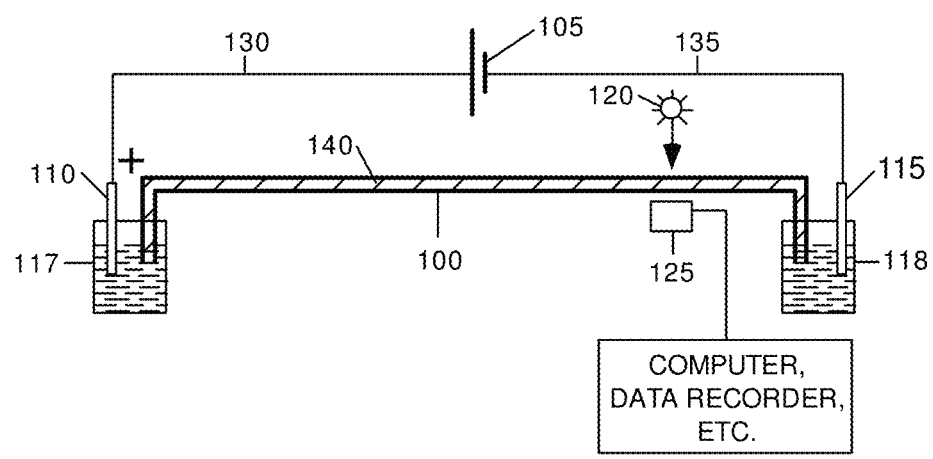
Fig. 2--Prior Art--Run
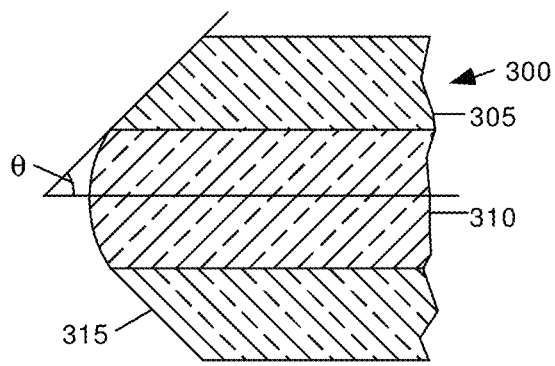
Fig. 3--Prior Art
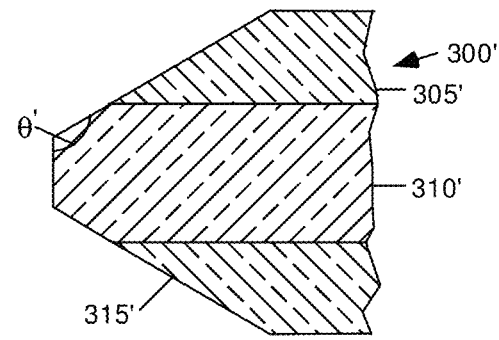
Fig. 4--Prior Art

LENSED OPTICAL FIBER FOR ILLUMINATING CAPILLARY TUBE

BACKGROUND

Prior Art—Elecrophoresis—FIGS. 1-4

Electrophoresis is a powerful and well-known method that is used in many fields of science to separate molecules having different sizes and different intrinsic electrical charges in order to analyze and synthesize chemical compounds. It is used in DNA sequencing, in the separation of mixtures of proteins, and the like. Two principal methods for performing electrophoretic separations are in routine use today.

Planar Gel Matrix:

The first method uses a planar gel matrix, such as agarose, with electrodes located at opposite edges of the gel. A mixture of ionized, i.e., charged, molecules is applied near the electrode on one edge of the gel, and an electrical potential is applied to the electrodes. Because of their intrinsic electrical charge the molecules are urged to move away from one electrode and toward the other one. The motion of the charged molecules is impeded by the structure of the molecules within the gel. The speed at which the charged molecules move depends upon their size, i.e., smaller molecules having a particular electrical charge move faster through the gel than larger ones with the same charge. Thus the difference in speeds results in separation of the previously mixed molecules. In most cases the various molecular species are not normally visible to the human eye. Prior to separation they are combined with dye molecules or tagged with radioactive atoms in well-known fashion, thus rendering them visible either by direct visual inspection or through the exposure of photographic film, respectively. Analysis of this separation is used to quantify the size and numbers of molecules contained in the original mixture.

Capillary Electrophoresis:

The second method, capillary electrophoresis (CE), is used by analytical chemists to separate ionic species from mixtures of chemical compounds. Instead of the planar arrangement described above, CE employs a narrow tube (capillary) through which the molecules move as they are separated.

FIGS. 1 and 2 are schematic drawings of a prior-art apparatus for performing a CE separation and an on-capillary detection. On-capillary means the point at which the separation is detected is in a section of the tube or capillary that is used in the actual separation, i.e., there is no interruption from the separation conduit to the detection cell. The apparatus comprises a capillary tube 100, a source of electrical potential 105, an anode 110, and a cathode 115. Cathode 115 and anode 110 are respectively connected to source 105 by electrical conductors 135 and 130. A light source 120 and a detector 125 are arranged so as to shine light through tube 100. Tube 100 is filled with a matrix substance such as a buffer solution 140, i.e., one that resists changes in pH when small quantities of a base or acid are added to it. The ends of capillary tube 100 are inserted into solutions contained in vials or other containers 116, 117, and 118. Capillary tube 100 is typically made of glass or quartz and has a bore (internal diameter) ranging between 50 and 100 microns, an outer diameter of 200-360 microns, and a length of 20 to 50 cm, although other sizes are used.

FIG. 1 shows the apparatus being loaded with a sample mixture 145 of an ionic species, such as biological molecules, having an intrinsic electrical charge. In this case, the intrinsic electrical charge of the molecules is positive so that they will move away from anode 110 toward cathode 115 as they are separated. If the intrinsic molecular charge is known to be negative, the electrical source polarity would be reversed, or the sample can be introduced at the cathode. The right-hand end of capillary 100 and cathode 115 are immersed in a buffer solution 140 in vial 118.

To load sample 145, electrical source 105 and light source 120 are de-energized. Vial 116 containing a solution of sample 145 to be separated is positioned so that anode 110 and the left-hand end of capillary 100 are immersed in sample solution 145. A small amount of the sample is urged into capillary 100 either using hydrostatic pressure or a brief application of electrical potential from source 105, in well-known fashion. After introduction of the sample, vial 116 is removed and replaced with vial 117 (FIG. 2) so that, prior to separation, the sample forms a band in a uniform matrix.

FIG. 2 shows the prior-art apparatus of FIG. 1 in use. Electrical source 105 and light source 120 are energized. Detector 125, such as a photodiode or photomultiplier tube, is connected to a computer 200 or other data recorder. The electric field established between anode 110 and cathode 115 within matrix 140 in capillary tube 100 urges the molecular components comprising sample 145 (FIG. 1) to move toward the cathode. As explained above, the smaller molecules move faster within matrix 140 and are thus separated from the slower-moving larger molecules. Light source 120 and detector 125 are located near cathode 115 since separation of the molecular species will be greatest at that location. Light source 120 emits a predetermined wavelength or band or bands of wavelengths of light of known intensity. Light from source 120 is arranged to shine through matrix 140 in capillary tube 100 and then onto detector 125. When illuminated, the molecules in sample 145 either absorb or absorb and re-emit light that is captured by detector 125. Intensities of the incident light from source 120 and the light reaching detector 125 are compared and recorded in computer 200 for later analysis. Sample concentration is calculated using a well-known formula, the Beer-Lambert law, explained, e.g., under "Beer-Lambert Law" in the Internet encyclopedia Wikipedia.

Light from source 120 that falls on matrix 140 within capillary 100 must be as bright as possible in order to maximize detection sensitivity of the apparatus. Thus source 120 is a critical part of this apparatus. Its intensity determines the dynamic range over which the apparatus operates. With higher intensity, greater the signal-to-noise ratio and linearity can be achieved in measurements.

The following is a list of some possibly relevant prior art that shows such light sources. Following this list I provide a discussion of these references.

| U.S. Patents | | | |
|---|---|---|---|
| Patent or Pub. Nr. | Kind Code | Issue or Pub. Date | Patentee or Applicant |
| 3,910,677 | A1 | Oct. 07, 1975 | Becker et al. |
| 5,037,199 | A1 | Aug. 06, 1991 | Hlousek |
| 5,239,360 | A1 | Aug. 24, 1993 | Moring et al. |
| 5,455,879 | A1 | Oct. 03, 1995 | Modavis et al. |
| 5,845,024 | A1 | Dec. 01, 1998 | Tsushima et al. |
| 6,317,550 | B2 | Nov. 13, 2001 | Irie et al. |
| 6,597,835 | B2 | Jul. 22, 2003 | Jie et al. |

Non-Patent Literature

Bruno, A. E. et al., "Theoretical considerations on the design of cylindrical flow cells utilizing optical fibres", Analytica Chimica Acta, 234 (1990) 259-262.

References that Show Light Input to an Optical Fiber from a Source Such as a Laser Becker shows a hyperbolic type optical fiber lens coupler that couples an optical fiber to an optical line source such as a laser diode. A cylindrical lens is used at the input end of an optical fiber in order to increase light collection and thereby coupling efficiency. The lens has a curved (hyperbolic) middle portion and two slanted side portions. Although Becker does not state a core diameter, he does state that his system is used in communications systems. For telecommunications applications, a single-mode optical fiber is required, in which the core diameter must be 10 microns or less.

Modavis shows a wedge-shaped, anamorphic micro-lens with two pairs of slanted surfaces formed at the end of a single-mode optical fiber that collects light from a laser. Modavis's mode field width, i.e. the effective width of light propagation in his fiber, is about 2 microns; the core width would be somewhat less.

Tsushima shows a manufacturing process for making tapered elliptic and cylindrical lenses for coupling to light sources such as laser diodes and light-emitting diodes. Tsushima's core diameter is about 6 microns.

Irie shows a wedged lens at the end of an optical fiber for coupling to a laser beam. The lens has a plane portion $2d$, perpendicular to the axis of the fiber, in the middle of the fiber and two symmetrical slant portions on the sides of the fiber. Irie's plane portion has a width of 1, 2, 4, or 6 microns or μm as indicated in Irie's FIG. 3.

Jie shows a wedged lens at the end of an optical fiber having a substantially flat portion formed at the end of the fiber core, two slant portions formed at the end of the fiber cladding, and curved portions between the flat and slanted portions. Jie's core diameter is 6 microns.

The small core diameter of the fibers used in these references is optimal for each of their purposes, i.e. the single-mode light propagation. However, the small core diameters severely limit the amount of light that can be emitted from one end of the fiber even if the other end of the fiber were illuminated by the brightest of sources.

References that Show Light Output from an Optical Fiber that is Used to Illuminate a Capillary Tube Hlousek and Moring both show the use of a ball lens to focus light on the inner channel of a capillary. Although the use of a ball lens increases light intensity within the capillary, the spherical aberration associated with a ball lens compromises the linear range of detection available in such a system.

Bruno shows the use of a flat-end optical fiber to illuminate a capillary, with no focusing lens between them. Although simple, the absence of a lens significantly reduces the amount of light that can be applied to the sample through the small fiber, because the size of the fiber must be smaller than the inner capillary channel. As a result, the signal-to-noise ratio of this apparatus is compromised.

The above-described references are each useful for their intended purposes. However each has one or more disadvantages as noted.

SUMMARY

I have discovered a new method for illuminating the capillary cores in an on-capillary CE apparatus. The need for a ball lens is eliminated, the light output is improved over that supplied by a flat-ended fiber, and a larger fiber with a different end configuration than those for use in telecommunications is used. In various aspects, the light-emitting end of an optical fiber is formed into predetermined shapes that permit a moderately-sized light source to properly illuminate the core of a CE capillary.

DRAWING FIGURES

Figures 6, 6A:
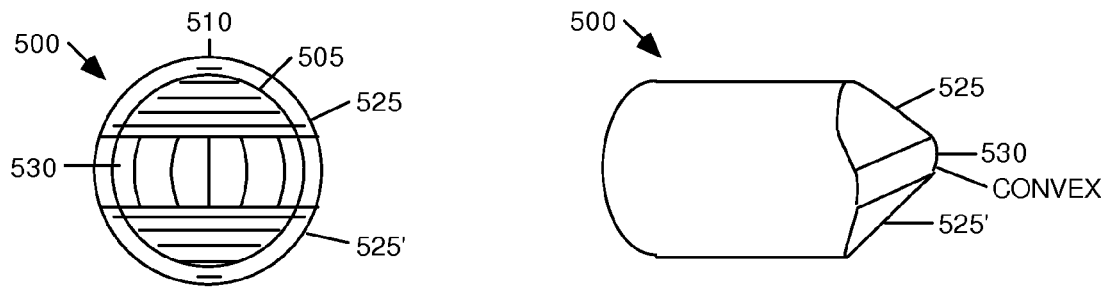
Figure 7:
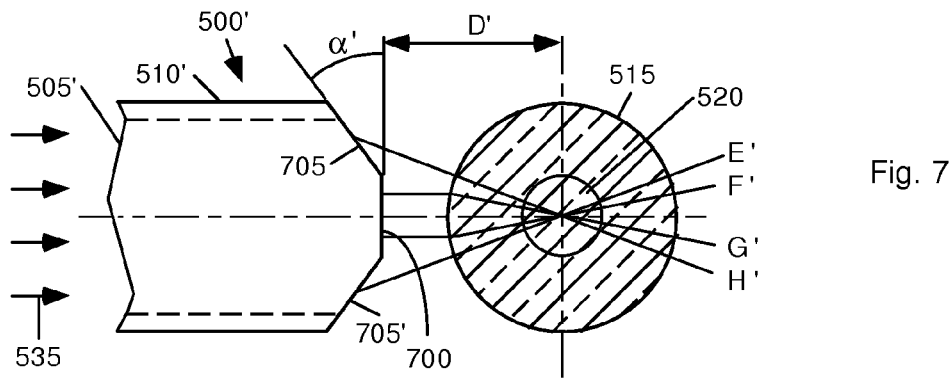
Figures 8, 8A:
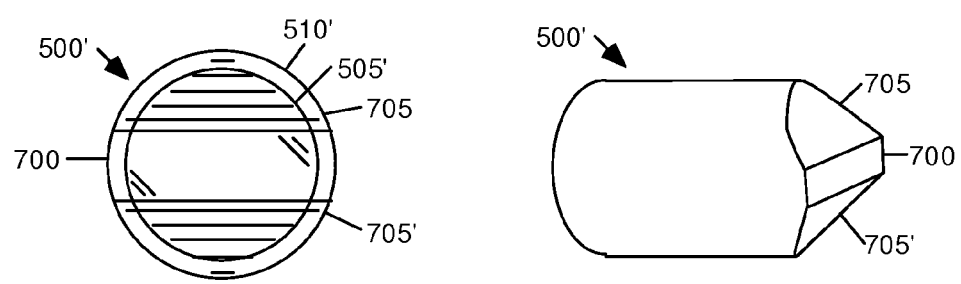
Figure 9:
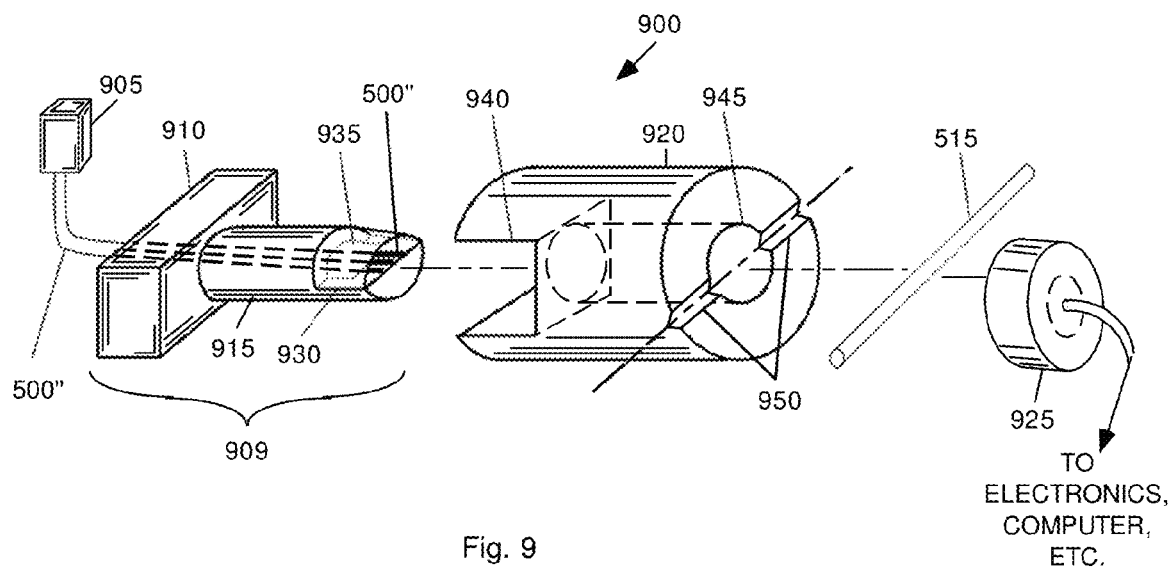

FIGS. 1 and 2 show a prior art CE system.
FIGS. 3 and 4 show two prior-art light collecting fibers.
FIGS. 5, 6, and 6A show side, end, and perspective outline views, respectively, of one aspect of an embodiment.
FIGS. 7, 8, and 8A show side, end, and perspective outline views, respectively, of a different aspect of the embodiment of FIGS. 5-6A.
FIG. 9 shows a perspective view of one aspect of an on-capillary absorbance detector apparatus incorporating the embodiments shown in FIGS. 5 through 8A.

| DRAWING REFERENCE NUMERALS | | | |
|---|---|---|---|
| 100 | Capillary tube | 105 | Electrical source |
| 110 | Anode | 115 | Cathode |
| 120 | Light source | 125 | Detector |
| 130 | Conductor | 135 | Conductor |
| 140 | Matrix | 145 | Sample |
| 200 | Computer | 300 | Optical fiber |
| 305 | Cladding layer | 310 | Core |
| 315 | Slope | 500 | Optical fiber |
| 505 | Core | 510 | Cladding |
| 515 | Capillary | 520 | Bore |
| 525 | Sloped region | 530 | Convex region |
| 700 | Flat region | 705 | Flat region |
| 900 | Absorbance detector apparatus | 905 | Light source |
| 909 | Terminal | 910 | Block |
| 915 | Tube | 920 | Cover |
| 925 | Photodetector housing | 930 | Platform |
| 935 | Epoxy | 940 | Channel |
| 945 | Bore | 950 | V-Groove |

DESCRIPTION

Brief Discussion of Prior Art for Illuminating Fibers—FIGS. 3 and 4

FIGS. 3 and 4 show two optical fibers that are formed according to Becker and Irie, supra, respectively. These two are representative of the remaining light collecting references. These references show variations in the means for coupling light from a source, such as a laser or light-emitting diode (LED), into an optical fiber. In all cases, the ends of the fibers are ground, polished, and formed to various geometries.

FIG. 3 shows a cylindrical lensed optical fiber 300 of Becker comprising an outer cladding layer 305 and an inner core 310, and having a circular cross-section. Core 310 is ground to a "substantially hyperbolic cylinder type optical coupling surface", while cladding layer 305 is ground to a slope 315 at a predetermined angle θ with respect to the axis of optical fiber 300.

FIG. 4 shows the cylindrical lensed optical fiber 300' of Irie comprising an outer cladding layer 305' and an inner core 310'. In this case, the end of optical fiber 300' is ground to a taper or slope 315' at an angle θ' and core 310' extends a predetermined distance outside cladding 305'. The remaining references show variations on the theme of grinding and polishing the ends of optical fibers for use as light collectors from lasers and LEDs.

DESCRIPTION

First Aspect of Embodiment—FIGS. 5 and 6

FIGS. 5 through 8A show two aspects of an optical fiber for illuminating a portion of the core of a CE capillary according to a first embodiment. FIGS. 5, 6, and 6A show a first aspect, specifically side, front, and perspective outline views of a round cylindrical optical fiber 500 that has a central core 505 and cladding 510. The boundary between core 505 and cladding 510 is indicated by dashed lines. The right end of fiber 500 comprises a lens or lensed region with a rectangular convex end or region 530 (FIG. 6A) and two generally triangular sloped regions 525 and 525' which extend back from region 530. As shown in FIG. 6A, regions 525, 525', and 530 are discrete and each faces in a different direction.

A CE capillary tube 515 (FIG. 5) with an inner bore 520 is positioned a predetermined distance D from optical fiber 500. The axis of tube 515 (including its bore 520) is oriented perpendicular to optical fiber 500 as shown. The diameter of core 505 of optical fiber 500 is typically 100-200 microns and is much larger than the diameter of bore 520 of capillary 515, which typically is 50-100 microns, although other sizes can be used.

In the aspect shown in FIGS. 5-6A, and as shown in FIG. 9, the light emitted from the end of optical fiber 500 is focused on a part of capillary 515 between the ends thereof. Fiber 500 is formed into three regions: a convex region 530 with radius r, and two sloped flat regions 525 and 525' that are formed at an angle α and are symmetrical to the axis of fiber 500. As shown best in FIGS. 5 and 7, regions 525 and 525' are sloped or slanted with respect to the axis of fiber 500 and the perpendicular line to such axis. I.e., regions 525 and 525', being sloped or slanted, lie between but not at 0 and 90 degrees to the axis of fiber 500 and the perpendicular to axis 500. The extent of convex region 530 between flat regions 525 and 525' is approximately the same as the diameter of bore 520 of capillary 515, typically 50-100 microns, although values ranging from 0.5 to 2 times the diameter of bore 520 can be used. The radius of curvature r is selected to place the focal point of convex region 530 at the central axis of bore 520 of capillary 515. Thus radius r is determined by the predetermined distance D between optical fiber 500 and capillary 515. Angle α is also selected to place the light ray from the middle of sloped flat regions 525 and 525' within or very near to the center of bore 520 of capillary 515. Typically, radius r is 100-150 microns and angle α is 20-30 deg., although other dimensions can be used. If angle α is greater than 42°, total internal reflection will occur within optical fiber 500 and this will reduce the amount of light leaving optical fiber 500. Light from a source such as 905 (FIG. 9) entering the left-hand end of fiber 500 is indicated by arrows 535. Focused light leaving the right-hand end of fiber 500 and passing through capillary 515 is identified by a plurality of rays E, F, G, and H.

Second Aspect of First Embodiment—FIGS. 7 and 8

FIGS. 7-8A show side, end, and perspective outline views, respectively, of a second, alternative aspect which is similar to that of FIGS. 5-6A but in which the end of optical fiber 500' that is focused on capillary tube 515 is formed into three flat regions. A first flat region 700 is located between second and third flat regions 705 and 705', respectively, and extends between regions 705 and 705' a distance equal or smaller than the diameter of bore 520 of capillary 515, although a range of thicknesses from 0.5 to 2 times the diameter of bore 520 can be used. Second and third flat regions 705 and 705', respectively, traverse core 505' and cladding 510' and are both ground at an angle α', symmetrical to the axis of core 500'. As in the previous aspect, angle α' is selected to place the light ray from the middle of sloped flat regions 705 and 705' of optical fiber 500' within or very near to bore 520 of capillary 515. If angle α' is greater than 42 deg, total internal reflection within optical fiber 500' will reduce the amount of light leaving optical fiber 500'. Light entering the left-hand end of fiber 500' is indicated by arrows 535. Focused light leaving the right-hand end of fiber 500' and passing through capillary 515 is identified by a plurality of rays E', F', G', and H'.

In the aspects shown in FIGS. 5 through 8A, the angles α and α' are typically 20-30 degrees and cannot go beyond 42 degrees, while in the prior art fiber optics discussed above the slope angles, converted to α and α' for comparison, lie typically between 40 and 50 degrees. In addition, the present optical fiber has a core diameter of 100-200 microns, while the prior-art fibers have core diameters of 10 microns or less.

Flat surfaces 525, 700, and 705 and curved surface 530 are ground using an abrasive wheel (not shown) or other similar arrangement. Methods for forming these surfaces are discussed in the cited prior art, such as Becker, Modavis, and Jie, and will not be discussed further here.

Capillary 515 and optical fiber 500 are made of glass or quartz, although other materials including plastics can be used. Light 535 can be white light comprising many wavelengths, or it can contain only one or a few selected wavelengths ranging from ultraviolet through the visible to infrared. Sources for this light can be light-emitting diodes, gaseous discharge tubes, arc lamps, incandescent lamps, plasma discharges, and the like. Sources with a range of wavelengths can be filtered to deliver one or a few wavelengths, if required. The material from which capillary 515 and optical fiber 500 are made is selected to pass, i.e., not attenuate, the wavelength of light in use. In some cases light 535 of one wavelength is used to stimulate fluorescence of a second wavelength within the sample in bore 520 of capillary 515. The materials from which capillary 515 and optical fiber 500 are made are well-known and take these considerations into account.

Operation

First Embodiment—FIG. 9

FIG. 9 shows an exploded perspective view of one aspect of the above embodiments in use. An exemplary absorbance detector apparatus 900 comprises a light source 905 and optical fibers 500". One or more fibers is used, generally less than four. The fibers extend through a block 910 which connects to a tube 915, both of which form a terminal 909. A cover 920 is fitted over terminal 909 and all of the foregoing elements are positioned on one side of capillary 515 as stated. A photodetector housing 925 is positioned on the other side of capillary 515. Absorbance detector apparatus 900 (other than the light source and optical fibers) is opaque and made of metal, plastic, or wood.

Tube 915 terminates at its left-hand end in block 910. At the right-hand end of tube 915 is a platform 930 to which one or more of optical fibers 500" are secured by a layer of epoxy 935. Optical fibers 500" are secured within block 910 and are then secured to light source 905. Optical fibers 500 are all oriented perpendicularly to bore 520 of capillary 515 as shown in FIGS. 5 and 7.

Cover 920 has an open channel 940 at its left-hand end and a central bore 945. A pair of V-grooves 950 are formed into the right-hand end of cover 920 across its diameter. Block 910 and tube 915 are sized to slidably fit into cover 920. V-grooves 950 are sized to mate with capillary 515. Capillary 515 is fixedly seated in grooves 950 (not shown) when photodetector housing 925 is urged against the right-hand end of cover 920 and secured there in well-known fashion, usually by screws or a clamp arrangement. Two grooves are used since capillary 515 is normally flexible and must be supported on both sides of bore 945.

Terminal 909 is then fully inserted into cover 920. End 530 of optical fiber 500 (FIG. 5) or end 700 of optical fiber 500' (FIG. 7) is thus held at a predetermined distance from capillary 515 to ensure that distance D or D' (FIGS. 5 and 7), respectively, is maintained. Thus when absorbance detector apparatus 900 is fully assembled, optical fibers 500 are secured at the proper distance from capillary 515.

Once assembled, absorbance detector apparatus 900 can be firmly secured by a clamp (not shown) or other means.

The assembly of terminal 909 and cover 920 thus position, align, and maintain the proper distance between the end of optical fiber 500 (or 500') and capillary 515.

CONCLUSIONS, RAMIFICATIONS, AND SCOPE

I have provided an improved lensed optical fiber for use in on-capillary detection apparatus. My design is an improvement over a flat-ended fiber and it does not require a separate lens, such as a ball lens, to properly direct light into the bore of a CE capillary for use in evaluating electrophoretic separations. Because the end of my optical fiber is shaped into a lens, a large core fiber can be used to efficiently illuminate a capillary without an additional lens.

While the above description contains many specificities, these should not be construed as limitations on the scope, but as exemplifications of some present embodiments. Many other ramifications and variations are possible within the teachings herein. For example, optical fibers made of a variety of formulations of plastic, glass, and quartz can be used. The optical fibers can have predetermined colors and they can range in length from a few millimeters to many meters. In absorbance detector apparatus 900, various changes can be made, such as eliminating open channel 940 and using a manual alignment and bond, and making block 910 and platform 930 perpendicular. My lensed optical fiber can also be used to quantify liquid chromatographic separations performed within translucent capillaries.

Thus the scope should be determined by the appended claims and their legal equivalents, rather than the examples and particulars given.

The invention claimed is:

1. A lensed optical fiber for illuminating a bore of a predetermined capillary tube, where said bore has an axis, comprising:
   an optical fiber having first and second ends and an axis,
      said optical fiber being arranged to conduct light applied to said first end to said second end and emit said light from said second end,
   said optical fiber having a core and a cladding layer, said core having a diameter of at least 50 microns,
   said second end having a predetermined shape comprising first and second flat regions and a third region disposed between said first and said second flat regions,
   said third region being selected from the group consisting of curved and flat regions, said third region, when curved, having a predetermined radius of curvature,
   said first and said second flat regions being sloped or slanted with respect to said axis of said optical fiber and also being sloped or slanted at an angle of less than 42 degrees with respect to a perpendicular line drawn to said axis of said optical fiber,
   said first, second, and third regions being discrete and each facing in a different direction,
   said third region having an extent between said first and said second flat regions that is smaller than the diameter of said core of said optical fiber and between 0.5 and 2 times the diameter of said bore of said capillary tube,
   whereby when said optical fiber is illuminated at said first end by a light source, light will be conducted by said optical fiber to said second end of said optical fiber and emitted from said first, second, and third regions and focused on said bore of said capillary tube.

2. The optical fiber of claim 1 wherein said angle of said first and said second flat regions of said optical fiber with respect to said perpendicular line is selected so that said light emitted from said first and said second flat regions of said optical fiber focuses on said bore of said capillary tube at a predetermined distance D between said optical fiber and said axis of said capillary tube.

3. The optical fiber of claim 1 wherein said third region of said optical fiber is curved and said predetermined radius of curvature of said third region is selected so that light emitted from said third region focuses on said bore of said capillary tube at a predetermined distance D between said optical fiber and said axis of said capillary tube.

4. The optical fiber of claim 1 wherein said optical fiber is made of materials selected from the group consisting of glass, plastic, and quartz.

5. The optical fiber of claim 1 wherein said light comprises at least one wavelength selected from the group consisting of infrared, visible, and ultraviolet wavelengths.

6. A method for illuminating a bore of a capillary tube, where said bore has an axis, comprising:
   providing a capillary tube,
   providing an optical fiber with first and second ends and an axis,
      said optical fiber having a core and a cladding layer,
      said core having a diameter of at least 50 microns,
      said second end of said optical fiber comprising first and second flat regions and a third region disposed between said first and said second regions,
      said third region being selected from the group consisting of curved and flat regions,
      said third region, when curved, having a predetermined radius of curvature,
      said first and said second flat regions being sloped or slanted with respect to said axis of said optical fiber and also being sloped or slanted at an angle of less than 42 degrees with respect to a perpendicular line drawn to said axis of said optical fiber, and
      said first, second, and third regions being discrete and each facing in a different direction,
   providing a light source arranged to shine light on said first end of said optical fiber,
   positioning said optical fiber a predetermined distance D from said axis of said capillary tube so that when said first end of said optical fiber is illuminated by said light source said optical fiber conducts light to said second end of said optical fiber, said light will be emitted and focused at said axis of said capillary tube, and
   orienting said optical fiber with respect to said axis of said bore of said capillary tube so that said flat regions are parallel to said axis of said capillary tube,
   whereby when said optical fiber is illuminated at said first end by a light source, light will be conducted by said optical fiber to said second end of said optical fiber and emitted from said first, second, and third regions and focused on said bore of said capillary tube.

7. The method of claim 6 wherein said angle of said first and second flat regions of said optical fiber with respect to said perpendicular line is selected so that said light emitted from said first and second flat regions of said optical fiber focuses on said bore of said capillary tube at a predetermined distance D between said optical fiber and said axis of said capillary tube.

8. The method of claim 6 wherein said third region of said optical fiber is curved and said predetermined radius of curvature of said third region is selected so that said light emitted from said third region focuses on said bore of said capillary tube at a predetermined distance D between said optical fiber and said axis of said capillary tube.

9. The method of claim 6 wherein said optical fiber is made of materials selected from the group consisting of glass, plastic, and quartz.

10. The method of claim 6 wherein said light comprises at least one wavelength selected from the group consisting of infrared, visible, and ultraviolet wavelengths.

11. The method of claim 6 wherein said light source is selected from the group consisting of lasers, light-emitting diodes, incandescent and gas-discharge light sources.

12. A lensed optical fiber for illuminating a bore of a capillary tube, where said bore has an axis, comprising:
   a source of light,
   an optical fiber having a circular cross-section, a predetermined diameter, first and second ends, and an axis, said optical fiber being arranged to conduct said light from said source of light, when said source of light is positioned to direct light at said first end of said optical fiber, to said second end and emit said light from said second end of said optical fiber,
   said optical fiber having a core and a cladding layer, said core having a diameter of at least 50 microns,
   said second end of said optical fiber having a predetermined shape comprising an end surface and first and second flat regions extending back from said end surface, said end surface constituting a third region disposed between said first and said second flat regions,
   said end surface of said third region having an extent between said first and said second flat regions that is smaller than the diameter of said core of said optical fiber and between 0.5 and two times the diameter of said bore of said capillary tube,
   said first and said second flat regions being sloped or slanted with respect to said axis of said optical fiber and also being sloped or slanted at an angle of less than 42 degrees with respect to a perpendicular line drawn to said axis of said optical fiber, and
   said first, second, and third regions being discrete and each facing in a different direction,
   whereby when said optical fiber is illuminated at said first end by a light source, light will be conducted by said optical fiber to said second end of said optical fiber and emitted from said first, second, and third regions and focused on said bore of said capillary tube.

13. The lensed optical fiber of claim 12 wherein said optical fiber is made of materials selected from the group consisting of glass, plastic, and quartz.

14. The lensed optical fiber of claim 12 wherein said light source is arranged to emit light comprising at least one wavelength selected from the group consisting of infrared, visible, and ultraviolet wavelengths.

15. The lensed optical fiber of claim 12 wherein said light source is selected from the group consisting of lasers, light-emitting diodes, incandescent, and gas-discharge light sources.

16. The lensed optical fiber of claim 12 wherein said end surface of said third region of said optical fiber is flat.

17. The lensed optical fiber of claim 12 wherein said end surface of said third region of said optical fiber is convex.

\* \* \* \* \*